United States Patent
Boecker et al.

(10) Patent No.: US 8,263,931 B2
(45) Date of Patent: Sep. 11, 2012

(54) METHOD FOR IDENTIFYING IN PARTICULAR UNKNOWN SUBSTANCES BY MASS SPECTROMETRY

(75) Inventors: Sebastian Boecker, Jena (DE); Florian Rasche, Jena (DE); Thomas Zichner, Chemnitz (DE)

(73) Assignee: Sebastian Boecker, Jena (DE)

( * ) Notice: Subject to any disclaimer, the term of this patent is extended or adjusted under 35 U.S.C. 154(b) by 0 days.

(21) Appl. No.: 13/145,501

(22) PCT Filed: Jan. 15, 2010

(86) PCT No.: PCT/DE2010/000054
§ 371 (c)(1),
(2), (4) Date: Jul. 20, 2011

(87) PCT Pub. No.: WO2010/083811
PCT Pub. Date: Jul. 29, 2010

(65) Prior Publication Data
US 2011/0278449 A1 Nov. 17, 2011

(30) Foreign Application Priority Data
Jan. 21, 2009 (DE) .................. 10 2009 005 845

(51) Int. Cl.
*H01J 49/00* (2006.01)
*H01J 49/26* (2006.01)
*B01D 59/44* (2006.01)
(52) U.S. Cl. ......... 250/282; 250/281; 250/284; 436/173
(58) Field of Classification Search .................. 250/282, 250/281, 284; 436/173
See application file for complete search history.

(56) References Cited

U.S. PATENT DOCUMENTS

| | | | | |
|---|---|---|---|---|
| 6,624,408 | B1 * | 9/2003 | Franzen | 250/282 |
| 6,747,272 | B2 * | 6/2004 | Takahashi | 250/282 |
| 7,197,402 | B2 | 3/2007 | Mistrik | |
| 7,271,384 | B2 * | 9/2007 | Sander | 250/282 |
| 7,820,378 | B2 * | 10/2010 | van den Boom et al. | 435/6.11 |
| 2003/0236636 | A1 | 12/2003 | Yoshinari et al. | |

(Continued)

FOREIGN PATENT DOCUMENTS

DE 103 58 366 7/2005

(Continued)

OTHER PUBLICATIONS

Shi, Peiying et al.; "Characterization and Identification of isomeric flavonoid O-diglyocosides from genus Citrus in negative electrospray ionization by ion trap mass spectrometry and time-of-flight mass spectrometry", Analytica Shimica Acta 598 (2007), pp. 110-118.

(Continued)

*Primary Examiner* — Nikita Wells
(74) *Attorney, Agent, or Firm* — Jordan and Hamburg LLP

(57) ABSTRACT

In order to use the mass spectrometrical analysis at the same time to determine the structure and/or families and/or the chemical properties of a substance, free of subjective evaluation, in the shortest amount of time, in an automatable fashion and with high accuracy, without requiring identical fragmentation patterns and/or defined comparison or identification rules, according to the invention a fragmentation graph is formed from one or more mass spectrometrical fragmentation spectra of the substance, the data of the graph being compared to reference data preferably stored in an electronic database. The invention is used in particular in biological, pharmaceutical and chemical applications for determining the structure and/or the family and/or the chemical properties of unknown substances.

17 Claims, 5 Drawing Sheets

$$C_8H_{11}NO_2 \geq C_8H_8O_2$$
$$C_8H_8O_2 \geq C_7H_8O$$
$$C_8H_8O_2 \geq C_8H_6O$$
$$C_8H_8O_2 \geq C_6H_4$$
$$C_7H_8O \geq C_6H_8$$
$$C_7H_8O \geq C_7H_6$$
$$C_7H_8O \geq C_6H_6$$
$$C_6H_8 \geq C_5H_4$$
$$C_7H_6 \geq C_6H_2$$
$$C_6H_6 \geq C_5H_2$$
$$C_5H_2 \geq C_3H_2$$

U.S. PATENT DOCUMENTS

2005/0192755 A1    9/2005    Nagalla et al.

FOREIGN PATENT DOCUMENTS

DE    10 2005 025 499    12/2006

OTHER PUBLICATIONS

Roessner, Ute et al.; "Simultaneous analysis of metabolites in potato tuber by gas chromatography-mass spectrometry", The Plant Journal (2000) 23(1), pp. 131-142.

Vogt, Leslie et al.; "Automated compound classification for ambient aerosol sample separations using comprehensive two-dimensional gas chromatography-time-of-flight mass spectrometry", Journal of Chromatography A, 1150 (2007), pp. 2-12.

ThermoFinnigan; Xclaibur; "Getting Productive: Protein and Peptide Analysis with BioWorks 3.0", Revision A, XCALI-97047, Manual.

Boecker, Sebastian et al.; "Towards de novo identification of metabolites by analyzing tandem mass spectra."; Bioinformatics (Oxford, England) Aug. 15, 2008 LNKD-PUBMED: 18689839, vol. 24, No. 16, pp. I49-I55, XP002585411.

Dimaggio, Peter A. Jr., et al.; "De novo peptide identification via tandem mass spectrometry and integer linear optimization."; Analytical Chemistry Feb. 15, 2007 LNKD-PUBMED: 17297942, vol. 79, No. 4, pp. 1433-1446, XP002585412.

Bafna V., et al.; "On de novo interpretation of tandem mass spectra for peptide identification."; Annual Conference on Research in Computational Molecular Biology; Proceedings of the seventh annual international conference on Research in computational molecular biology, Apr. 10, 2003, pp. 9-18, XP002585399.

Klagkou, Katerina et al.; "Approaches towards the automated interpretation and prediction of electrospray tandem mass spectra on non-peptidic combinational compounds", Rapdi Commun. Mass Spectrom. 2003; 17: pp. 1163-1168.

Jiang, Tao et al.; "Alignment of trees—an alternative to tree edit", Theoretical Computer Science 143 (1995) pp. 137-148.

Kertesz, Tzipporah M. et al.; "CE50: Quantifying Collision Induced Dissociation Energy for Small Molecule Characterization and Identification", J. Am. Soc. Mass Spectrom, Sep. 2009, 20 (9), pp. 1759-1767.

* cited by examiner

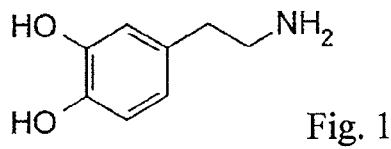
Fig. 1
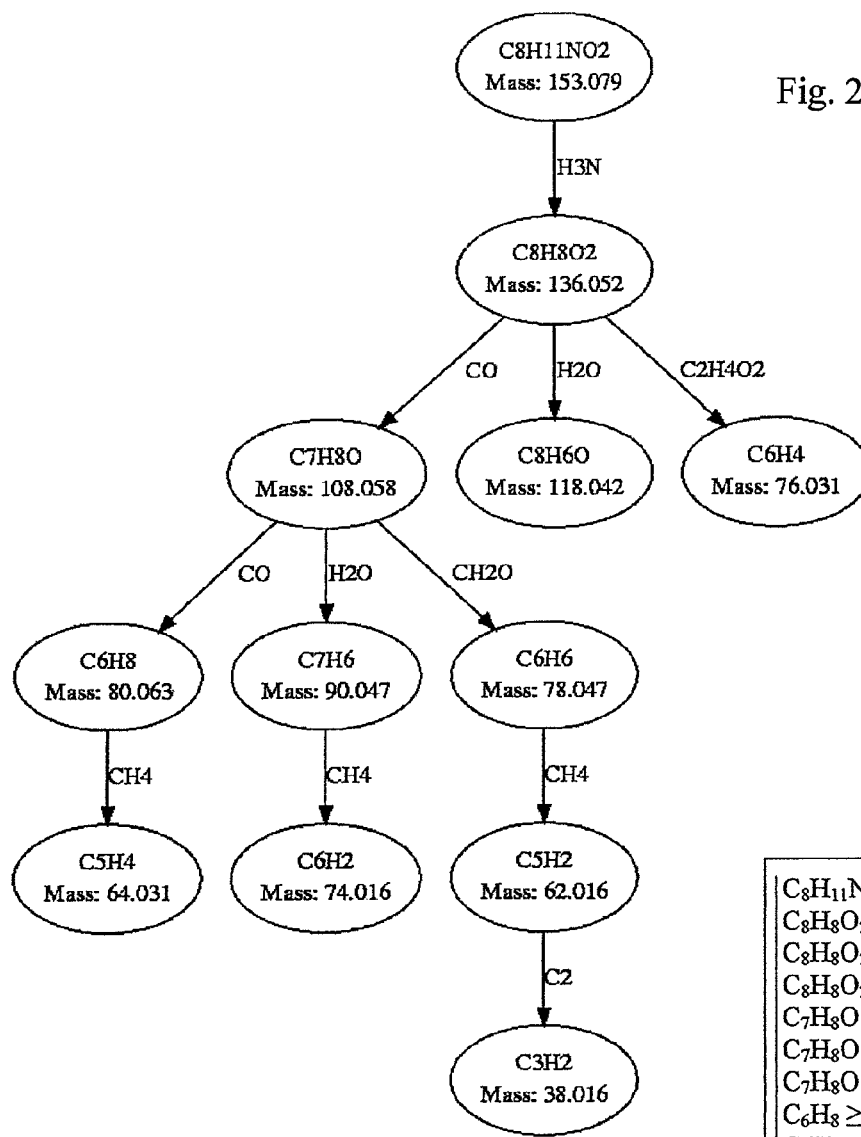
Fig. 2
Fig. 3

| Position | Bewertung | Klasse | Substanz |
|---|---|---|---|
| 1 | 31 | a | tryptophane |
| 1 | 31 | a | citrulline |
| 3 | 25 | a | arginine |
| 4 | 23 | a | tyrosine |
| 5 | 20 | a | asparagine |
| 6 | 19 | u | tyramine |
| 6 | 19 | u | dopamine |
| 8 | 17 | a | threonine |
| 8 | 17 | a | glutamic acid |
| 10 | 15 | a | phenylalanine |
| 11 | 14 | c | cafeoyl choline |
| 11 | 14 | a | cystine |
| 13 | 13 | u | 6-aminocapronic acid |
| 13 | 13 | a | cysteine |
| 15 | 12 | a | methionine |
| 16 | 10 | u | spermine |
| 17 | 9 | c | vanilloyl choline |
| 17 | 9 | c | 4-hydroxybenzoyl choline |
| 17 | 9 | c | 4-hexosyloxybenzoyl choline |
| 20 | 7 | c | Syringoyl choline |
| 20 | 7 | c | feruloyl choline |
| 20 | 7 | c | cinnamoyl choline |
| 20 | 7 | c | benzoyl choline |
| 20 | 7 | c | 4-hexosylvanilloyl choline |
| 20 | 7 | c | 4-hexosyloxycinnamoyl choline |
| 20 | 7 | c | 4-coumaroyl choline |
| 20 | 7 | a | aspartic acid |
| 28 | 6 | a | glutamine |
| 28 | 6 | a | alanine |
| 30 | 5 | c | sinapoyl choline |
| 30 | 5 | c | 4-hexosylferuloyl choline |
| 32 | 4 | c | 3-(4-hexosyloxyphenyl)propanoyl choline |
| 33 | 2 | u | unknown |
| 34 | 0 | u | spermidine |
| 34 | 0 | c | acetyl choline |

Klassifikation:
a – Aminosäure; c – Cholin; u – Nicht klassifiziert

Fig. 8

| Position | Bewertung | Klasse | Substanz |
|---|---|---|---|
| 1 | 40 | c | 4-hexosyloxycinnamoyl choline |
| 2 | 33 | c | 3-(4-hexosyloxyphenyl)propanoyl choline |
| 3 | 29 | c | cafeoyl choline |
| 3 | 29 | c | 4-hydroxybenzoyl choline |
| 5 | 26 | c | 4-hexosylvanilloyl choline |
| 6 | 24 | c | vanilloyl choline |
| 7 | 22 | c | Syringoyl choline |
| 7 | 22 | c | feruloyl choline |
| 7 | 22 | c | cinnamoyl choline |
| 7 | 22 | c | benzoyl choline |
| 7 | 22 | c | 4-coumaroyl choline |
| 12 | 19 | c | 4-hexosylferuloyl choline |
| 13 | 15 | c | sinapoyl choline |
| 14 | 14 | u | dopamine |
| 14 | 14 | a | tyrosine |
| 14 | 14 | a | asparagine |
| 17 | 13 | a | tryptophane |
| 18 | 12 | a | glutamic acid |
| 18 | 12 | a | aspartic acid |
| 20 | 9 | u | unknown |
| 20 | 9 | u | tyramine |
| 20 | 9 | u | spermine |
| 20 | 9 | u | 6-aminocapronic acid |
| 20 | 9 | a | threonine |
| 20 | 9 | a | phenylalanine |
| 20 | 9 | a | methionine |
| 20 | 9 | a | histidine |
| 20 | 9 | a | cystine |
| 20 | 9 | a | cysteine |
| 20 | 9 | a | citrulline |
| 20 | 9 | a | arginine |
| 32 | 6 | u | spermidine |
| 33 | 2 | a | glutamine |
| 33 | 2 | a | alanine |
| 35 | 0 | c | acetyl choline |

Klassifikation:
a – Aminosäure; c – Cholin; u – Nicht klassifiziert

Fig. 9

METHOD FOR IDENTIFYING IN PARTICULAR UNKNOWN SUBSTANCES BY MASS SPECTROMETRY

BACKGROUND OF THE INVENTION

The invention relates to a method for identifying chiefly unknown substances by mass spectroscopy to determine the structure and/or families and/or the chemical properties of said substances.

Mass spectrometry is one of the currently most common methods for analyzing chiefly unknown substances (for example J. H. Gross: Mass Spectrometry: A Textbook, Springer publishing house Berlin, 2004).

Mass spectrometry allows precise determination of the molecular mass of the analyzed substance. Furthermore, it is possible to fragment a is substance in the mass spectrometer once or several times, i.e. to break its chemical bonds. Subsequently, the masses of the fragments produced in this way will also be measured. As a result one or several fragmentation spectra are generated (also called daughter ion spectra).

However, it is problematic, particularly for unknown chemical compounds, to identify the structure and/or families and/or chemical properties of these compounds because only masses can be determined by mass spectrometry.

The original form of a lot of pharmaceuticals and other chemical substances used in industry and research is produced by living beings and has been discovered by chance or by a very complex search. Most of the substances produced by living beings are still completely unknown in research.

The method described hereinbelow can simplify the systematic search for potential active agents considerably by, for example, identifying all substance families of all small substances (lighter than 1500 dalton) that are contained in a biological sample. Afterwards, only those compounds must be analyzed more precisely that belong to the families which are relevant for the field of application.

The substance identification of pharmaceuticals and natural compounds is particularly interesting because of the high importance of these substances for medicine as well as pharmaceutical and biological research. Natural compounds are all substances that are contained in animate and inanimate nature, i.e. most of all in plants and animals but also in fossil deposits. Said natural compounds include, for example, all metabolites produced by chemical or enzymatic reactions, but also the decomposition products of substances that are added to nature by man, e.g. pharmaceuticals or environmental toxins. Even if natural compounds are probably the main field of application of the method described hereinbelow, the method is not restricted to them. The application of this method is also possible in other areas of chemistry, for example in materials science.

As natural compounds mainly exist as mixtures (e.g. cell extract, environmental sample) a separation procedure is often carried out before starting mass spectroscopy in order to separate the substances to be indentified for the mass spectrometrical analysis. Usually, this separation process is gas or liquid chromatography or capillary electrophoresis (for example U. Roessner, C. Wagner, J. Kopka, R. Tretheway, L. Willmitzer: Technical advance: simultaneous analysis of metabolites in potato tuber by gas chromatography-mass spectrometry, Plant J, 2000, 23, 131-142).

It is known (for example R. Mistrik: Xcalibur HighChem: Mass Frontier Software. HighChem/ThermoFinnigan, Manual 2001) to compare fragmentation patterns, which are determined by mass spectrometrical analysis, with idealized patterns, so called rules, that have been manually obtained from reference data. Such a comparison could be principally automated but it requires that the corresponding rules for the analyzed substance have been generated. Therefore, this method cannot be used at all for unknown substances. Moreover, these rule-based approaches cannot process error-containing data and consequently they are not useful in practical applications (K. Klagkou, F. Pullen, M. Harrison, A. Organ, A. Firth & G. J. Langley: Approaches towards the automated interpretation and prediction of electrospray tandem mass spectra of non-peptidic combinatorial compounds, *Rapid Commun Mass Spectrom,* 2003, 17, 1163-1168).

In the special case, in which a fragmentation spectrum that has been generated under the same measurement conditions has already an identical equivalent in a reference database, it would be possible to find the analyzed substance in a computational comparison by searching the identical spectrum in the reference database and to identify said substance in this manner (L. Vogt, T, Groeger & R. Zimmermann: Automated compound classification for ambient aerosol sample separations using comprehensive two-dimensional gas chromatography-time-of-flight mass spectrometry, *J Chromatogr A,* 2007, 1150, 2-12; DE 103 58 366 B4, U.S. Pat. No. 6,624,408 B1, US 2003 023 66 36 A1, U.S. Pat. No. 6,747,272 B2).

This method does not function for completely unknown substances because it requires a reference spectrum of the substance in the database. Furthermore, fragmentation spectra depend partly very much on external parameters and therefore they differ from lab to lab. Direct comparisons between spectra are not convincing in this case. Therefore, the search for an existing identical reference spectrum obtained under comparable conditions is only possible in very few applications.

To avoid the latter disadvantage it is also known to search fragment ions in a database where they are stored as defined fragmentation patterns (U.S. Pat. No. 7,197,402 B2). Either these ions must possess a known, clear structure or fragmentation spectra of these ions must be measured in an additional mass spectrometrical analysis. These spectra produced by multiple fragmentation ($MS^n$) should, as indicated, be more comparable than the 'single' fragmentation spectra mentioned before.

However, this procedure is also limited to the identification of known (and electronically saved) substances. Furthermore, the multiple fragmentation can only be performed by using very special types of mass spectrometers so that the additional efforts are further increased.

If substances are to be identified for which reference data or comparison or identification rules do not exist completely or do not exist at all, it will still be necessary, at least in individual cases, to evaluate smaller molecules on the basis of their fragmentation pattern, i.e. intensive investigations must be carried out to find out if comparable similarities to known structures can be found that could allow or at least support the determination of a substance family, the chemical properties or even the molecule structure (P. Shi, Q. He, Y. Song, H. Qu and Y. Cheng: Characterization and identification of isomeric flavonoid O-diglycosides from genus Citrus in negative electrospray ionization by ion trap mass spectrometry and time-of-flight mass spectrometry, *Anal. Chim. Acta,* 2007, 598, 110-118). However, this evaluation is subjective and time-consuming and it is based on human intuition. Therefore, it is not an objective and rapid substance identification but requires high expert knowledge and extensive experience in this field. Nevertheless, the hit ratio even for smaller molecules is not very high in practical applications. Moreover, the method cannot be automated for the aforementioned reasons. The evaluation of larger molecules by means of the described method would not be useful in practice, particularly due to the high demands placed on the expert and the expected low hit ratio.

In 2008, Boecker and Rasche (S. Boecker & F. Rasche: Towards de novo identification of metabolites by analyzing tandem mass spectra, *Bioinformatics,* 2008, 24, 149-155) have introduced a mathematical formalization of the concept of fragmentation patterns. In their method they used graphs to represent the fragmentation pattern of a substance. A graph should be an amount of objects, usually designated as nodes, and a set of pairs from the elements of this amount, usually designated as edges. This set of pairs represents the relations of the objects between each other. In this case, the fragments of the substance are represented as nodes and the fragmentation reactions are represented as edges. As the structure of the analyzed substance is not known, the nodes are marked with the total formulas of the fragments and the edges are marked with the total formulas of the neutral losses. These fragmentation graphs are used to determine the total formula of an unknown substance. However, total formulas alone are not sufficient to identify a substance and do not allow to determinate the family of the analyzed substance. A use of the proposed graphs of fragmentation patterns for identifying particularly unknown substances or for determining their family and/or chemical properties have not come to the attention of the experts either.

Furthermore, in a special biological or medical application the alignment of trees is known for comparing RNA structures (T. Jiang, L. Wang & K. Zhang: Alignment of trees: an alternative to tree edit, *Theor. Comput. Sci., Elsevier Science Publishers Ltd.,* 1995, 143, 137-148). In this method, the marked nodes of the trees to be compared are positioned on top of each other in such a manner that the markings differ as little as possible from each other. The trees must be identical in their structure; only so called gap nodes may be added in the branches of the tree presentation, if required. Applications of this method, particularly to identify substances or their family and/or chemical properties in mass spectrometrical analyses of said substances, are not known either.

SUMMARY OF THE INVENTION

The task of the invention was to be able to use the mass spectrometrical analysis, particularly of unknown chemical compounds for their identification, at the same time to determine the structure and/or family and/or the chemical properties of said substances, free of subjective evaluation, in an automatable fashion and with high accuracy, without requiring identical fragmentation patterns and/or defined comparison or identification rules.

According to the invention this aim is achieved by recording at least one mass spectrometric fragmentation spectrum (daughter ion spectrum) in the mass spectrometric analysis of a substance to be examined, and from said spectrum a fragmentation graph (that is hypothetical for unknown substances) is generated which is exclusively known so far for determining a total formula of a substance. The fragmentation graph is represented by objects and links of the at least one mass spectrometric fragmentation spectrum, for example by nodes as objects (fragments of the substance) and by edges (fragmentation reaction as a link). However, the presentation of the fragmentation graph for realizing said objects and links can also be a mathematical presentation that deviates from the typical expression by nodes and edges, for example a partial order, a relation, a hierarchy.

The data of this fragmentation graph are compared, preferably by the support of a computer, to existing reference data of fragmentation graphs of known substances. To do this, the arrangement for the mass spectrometric analysis is connected with a computer that has an access to an electronic database in which said reference data of the known fragmentation graphs are provided for the comparison. Thus, the data of the fragmentation graphs can be compared simultaneously and automatically parallel to the mass spectrometric analysis of the substance that is to be examined or identified. During the comparison of the data of the fragmentation graphs identical or at least similar partial graphs, i.e. a subset of the nodes and edges, are searched in order to determine the mass-spectrometrically analyzed substance on the basis of this known fragmentation graph or subset by using the substance structure and/or family and/or the chemical substance properties.

The computational data comparison allows an automatic substance identification in a very short time on the basis of a large number of known fragmentation graphs without necessarily requiring complete fragmentation graphs of the substance to be determined and/or defined comparison or identification rules for the comparison for reference purposes because the comparison does not consider the complete fragmentation spectrum but also substructures of said fragmentation graph.

All automatable and feasible methods known so far require that the substance to be analyzed is already known, has already been examined by mass spectrometry and is stored as a complete reference fragmentation pattern. Contrary to these (aforementioned) known methods the inventive procedure does not require that the substance to be identified is already contained in the reference data. It is sufficient that the data used for comparison show at least partially similarities of the complete or partial fragmentation graph compared with the fragmentation graph of the substance to be identified.

Thus, this method allows the automatic identification of completely unknown substances for the first time. Up to now, this was only possible manually.

Unlike time-consuming manual analyses the inventive method can realize the spectra without subjective requirements in real time, i.e. about as rapidly as the measurement itself (and therefore simultaneously with it).

By means of this innovation, the prompt analysis of typical mass spectrometrical test series with hundreds of substances is made possible. Furthermore, in this method the identification is based on objective criteria with high precision and not on human intuition.

The combination with other methods for automating the measurement and analysis of fragmentation graphs (e.g. DE 10 2005 025 499 B4 and DE 103 58 366 B4) would even allow the completely automatic performance and analysis of such a test series without any user intervention.

Thus, the fragmentation graph of the substance to be analyzed can be generated manually or automatically.

The data of the fragmentation graphs can be compared on a local or global basis, for example by pairwise or multiple alignments.

It is possible to record fragmentation spectra for generating the fragmentation graphs e.g. with a tandem mass spectrometer or by multiple fragmentation ($MS^n$). In such a process the fragmentation can be performed by collision induced dissociation (CID), electron transfer dissociation (ETD), electron capture dissociation (ECD), infrared multiphoton dissociation (IRMPD), blackbody infrared radiative dissociation (BIRD), higher-energy C-trap dissociation (HCD), in-source fragmentation or post-source decay (PSD).

Before recording the fragmentation spectra a substance separation can be advantageously performed by liquid chromatography, gas chromatography or capillary electrophoresis.

Apart from the inventive data comparison of the fragmentation graphs it can be practical to use further criteria for identifying the substance, particularly the chromatographic retention time and/or the electrophoretic thoughput time and/or UV absorption spectra.

A special potential application of the inventive method is based on clusters of substances to be identified. For this purpose, fragmentation spectra of three or more, but generally a higher number of substances, are measured and fragmentation graphs are calculated, e.g. in the method of Boecker and Rasche (S. Boecker & F. Rasche: Towards de novo identification of metabolites by analyzing tandem mass spectra, Bioinformatics, 2008, 24, 159-155). In this method, unknown or known substances, or generally known and unknown substances can be used. In the method described here pairwise similarities are calculated for these is fragmentation graphs so that a matrix of pairwise similarities is obtained. On the basis of such a similarity matrix methods for cluster analyses can be employed then. For doing this, all objects in one cluster should be similar to each other but they should show only a low degree of similarity with objects beyond the cluster. Generally, the cluster is analyzed in an automated process but a manual procedure is also possible. Any graph-theoretic, hierarchic, partitionizing, optimizing or other methods can be used for the cluster analysis, for example agglomerative clustering (e.g. UPGMA), k-means or k-nearest neighbors). On the basis of the calculated clusters conclusions can be drawn on the analyzed substances, if for example an unknown substance is clustered together with one or more known substances.

Another possible application of the inventive method is the combination of the similarity, which has been determined by the comparison of the fragmentation graphs, with other substance properties (measured or predicted). This can be done for the clustering process and also for all the other potential applications and fields described in the following. Other known substance properties are, for example, the mass of both substances, the mass difference between the substances, possible explanations of the mass difference by total formulas, number of peaks in the measured mass spectra, total formulas of the substances (hypothetical or validated), retention time, electrophoretic thoughput time, UV absorption spectra, or the $CE_{50}$ value of the substance (Kertesz, T. M., Hall, L. H., Hill, D. W. & Grant, D. F. CE50: quantifying collision induced dissociation energy for small molecule characterization and identification. J. Am. Soc. Mass Spectrom., 2009, 20, 1759-1767). One, several or even all of these further substance properties can be used for said combination.

Another possible application can use the similarity of fragmentation graphs for predicting the structural similarity of substances. The structural similarity of substances can be measured, for example, by a Tanimoto coefficient or Jaccard index. This structural similarity can be predicted, for example, by methods of supervised machine learning (e.g. support vector machines SVM, neural networks, decision trees, decision forests, naive Bayes). In these methods, the substances can be classified according to a structural similarity of e.g. 90% or more (alternatively 80%, 95% or another value) that is based on the similarity of the fragmentation graphs and other known substance properties.

Furthermore, the fragmentation similarity, combined with other substance properties, can be used for a direct prediction of the substance similarity (for example Tanimoto coefficient or Jaccard index). For this purpose, methods of direct machine learning, such as linear regression, SVM for regression (SVR), v-support vector regression (v-SVR) or local linear maps, can be used.

The invention can be advantageously used for a partial or complete determination of the structure of unknown substances by comparing fragmentation graphs. To do this, the fragmentation graphs of reference substances with known structure, which have a high local or global similarity with the fragmentation graph of the substance to be identified, can be used. Thus, the structure of the substance to be identified can be hypothesized and then evaluated, for example, by the application of further experimental techniques (multi-stage fragmentation mass spectrometry or NMR spectrometry). The hypotheses about the structure of the substance to be identified that are based on other experimental techniques can, in turn, be evaluated and verified by the comparison of fragmentation graphs.

One field of application of the invention is also the screening of unknown substances for potential biological active agents (bio-prospecting). For example, for a known active agent it is possible to search for substances that show a similar or identical effect (e.g. generic products). Moreover, substances can be searched for that show an improved effect or do not have one or more of the undesired side effects of the active agent. This technique can also be used for active agents that are not allowed or not suitable for the medication for human beings because, for example, severe side effects predominate over the desired effect of the active agent. For screening procedures the secondary metabolites of organisms, particularly of plants, fungi and bacteria, can be examined for example. Screening can be made under different exterior conditions, in different development phases and for different tissue types, for example semen, roots and leaves of a plant. The fragmentation mass spectra can be generated in an automatic process in which the substances to be fragmented can be determined, for example, automatically and without the knowledge about the substances contained in the sample. The application is not restricted to drugs or active agents that are used for human beings.

The examination of decomposition products of pharmaceuticals is also advantageous. In human metabolism the active agents and other substances are decomposed or transformed step by step. In a similar way pharmaceuticals can be decomposed or transferred by exterior influences (e.g. by improper storage, for example caused by too much heat). Here, it could be a possible task to find out the substances that are produced during the decomposition process and the effects and side effects that are caused by said substances.

An application of the inventive method is also possible for the identification of detectable substances, e.g. biomarkers. Environmental influences or foreign substances can change the metabolism of a biological system. It is for example possible to identify substances that are produced as a result of an infection. Laboratory blood tests can find out if such substances are contained in the patient's blood and possible inflammation factors can be deduced from the test result.

A further field of application of the inventive method is the identification of unknown drugs. For this purpose, the unknown substance is examined by mass spectrometry and its fragmentation graph is compared with the fragmentation graphs of known legal or illegal drugs as described above. In this way information can be gained about a possible drug effectiveness of the unknown substance.

The identification of performance-enhancing substances (doping) is also possible. New performance-enhancing substances are permanently developed and already known performance-enhancing substances are constantly improved and such new or improved substances can be identified by comparing the fragmentation graphs with known performance-enhancing substances.

Furthermore, the method can be used for identifying messengers (signaling molecules). Such messengers can exist within one cell, between different tissues or between organisms of one or more species, and they control the interaction of the cells in an organism. In plants such messengers serve, for example, to attract herbivores of plant pests that have infested plants. Such messengers can also cause the damage of a plant pest (allomones). The identification of said messengers can be used, for example, for the development of pesticides or for the cultivation of new plant species.

In addition to this it is possible to identify substances in drinking water, river water or other waters. To guarantee a high water quality it is necessary to identify the substances that are contained in the water, for example, to exclude a danger for men, animals and plants. These substances can be, for example, decomposition products of substances that have been introduced by men (e.g. hormones, pesticides) or substances that have been produced by microorganisms or metabolized substances.

A further field of application of the inventive method is the general identification of (unknown) metabolites for scientific or commercial purposes.

BRIEF DESCRIPTION OF THE DRAWINGS

The invention will be explained in more detail by virtue of the embodiments for determining structural similarities and for classifying substances as shown in the figures.

They show:

FIG. 1: Structural formula of dopamine

FIG. 2: Hypothetical fragmentation graph of dopamine in which the nodes correspond to the fragments measured by tandem mass spectrometry and the edges correspond to neutral losses FIG. 3: Fragmentation graph of dopamine, shown as a partial order

FIG. 8: Overview on the evaluation of the alignments with the hypothetical fragmentation graph of histidine FIG. 9: Overview on the evaluation of the alignment with the hypothetical fragmentation graph of 4-hexosyloxybenzoyl choline

Figure 4:
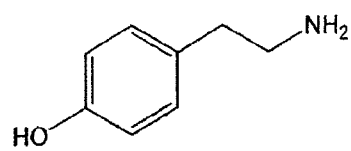
FIG. 4: Structural formula of tyramine

DETAILED DESCRIPTION OF THE INVENTION a) Determination of Structural Similarities:

The determination of the structural similarities of two or more substances is explained in the following using the substances dopamine and tyramine as an example. Both substances belong to the biogenic amines and have a very similar structure (see FIGS. 1 and 4).

In the typical application one of the two structures will be unknown. Then, assumptions about this structure can be made by means of this method. The example introduced here shall explain an approach for this task.

Both dopamine and tyramine have been examined by tandem mass spectrometry. The fragmentation was performed by means of collision induced dissociation (CID) known per se. However, it is also possible to use other mass spectrometry methods, e.g. $MS^n$, or other fragmentation techniques.

Figure 5:
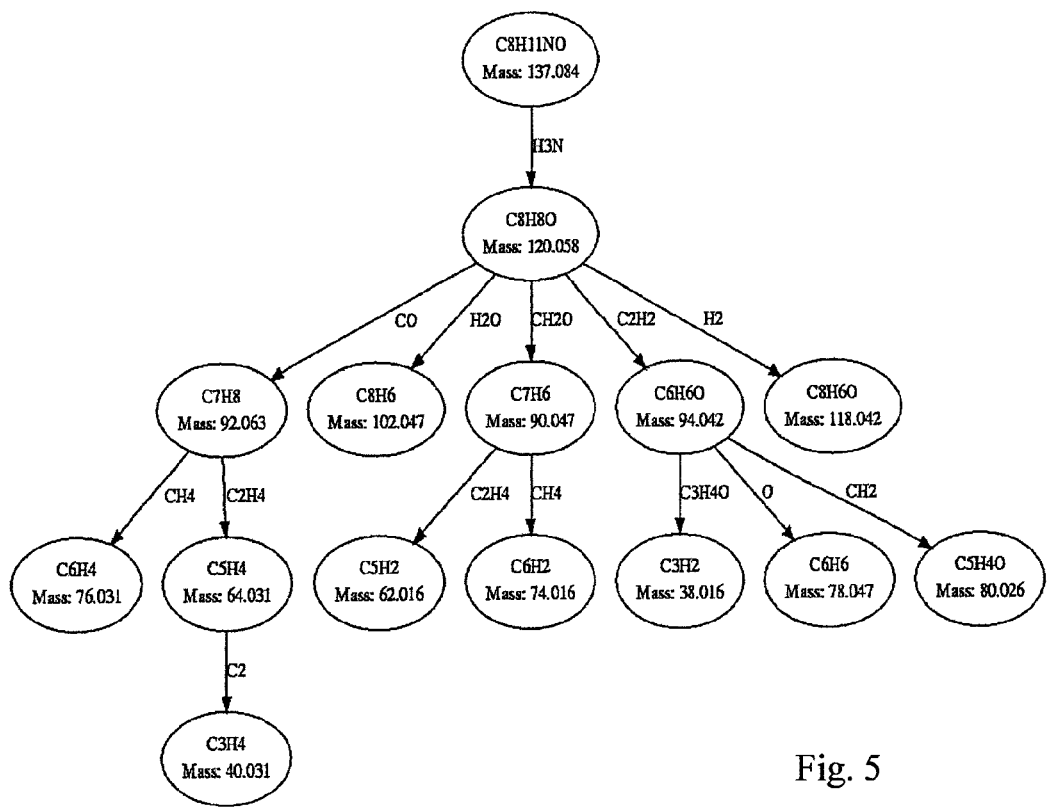
FIG. 5: Hypothetical fragmentation graph of tyramine, presented again as nodes (fragments) and edges (neutral losses)

Multiple fragmentation spectra (daughter ion spectra) have been measured for both substances and then hypothetical fragmentation patterns have been calculated. It also possible to use manually generated fragmentation patterns for the further analysis. The fragmentation graphs with the hypothetical course of the two fragmentations are shown in FIG. 2 (dopamine) and FIG. 5 (tyramine) with nodes as fragments of the substance and with edges as fragmentation reactions (neutral losses). Other possible presentations are, for example, partial orders (see FIG. 3), relations and hierarchies.

As a further step the two fragmentation graphs were edited for the comparison. The data relevant for this example are the neutral losses that are produced during the fragmentation (always indicated at the edges of the graphs). This information was transferred to the nodes, which are always positioned below them, because an algorithm was used afterwards for aligning the nodes of two graphs. If, however, both the fragments and the neutral losses or only the fragments are considered in the comparison or if algorithms are used for aligning the edges, this step is not necessary, but perhaps another edition of the fragmentation graphs could be useful or required.

The two edited fragmentation graphs of dopamine and tyramine have been locally aligned then. That means the areas of the two graphs that show the highest degree of similarity have been determined. As in this example the fragmentation graphs have been trees, the tree alignment algorithm according to T. Jiang, L. Wang & K. Zhang (Alignment of trees: an alternative to tree edit, *Theor. Comput. Sci., Elsevier Science Publishers Ltd.*, 1995, 143, 137-148) has been used. The evaluation of the node pairs has been selected as follows: Same nodes (i.e. nodes with the same total formula) have got a very positive evaluation in which the dimension of the neutral losses have been considered, too; node pairs for which the difference in the total formula could be explained by chemical facts have been assessed in a slightly positive manner, and pairs of different nodes as well as pairs consisting of one node and a gap have got a negative evaluation. At the end, the calculation of the total evaluation of an alignment has been based on the sum of all individual evaluations of the node pairs.

Apart from the approach selected in this example, numerous other possibilities exist for the evaluation of the node pairs, e.g. the calculation of log odds (logarithmized "chances") or log likelihoods (logarithmized probabilities). Furthermore, it is possible to determine the optimal evaluation function by means of machine learning or evolutionary algorithms.

An alignment can be made either locally (as in this example) or globally and multiple graphs can also be compared with each other simultaneously (multiple alignment).

Figure 6:
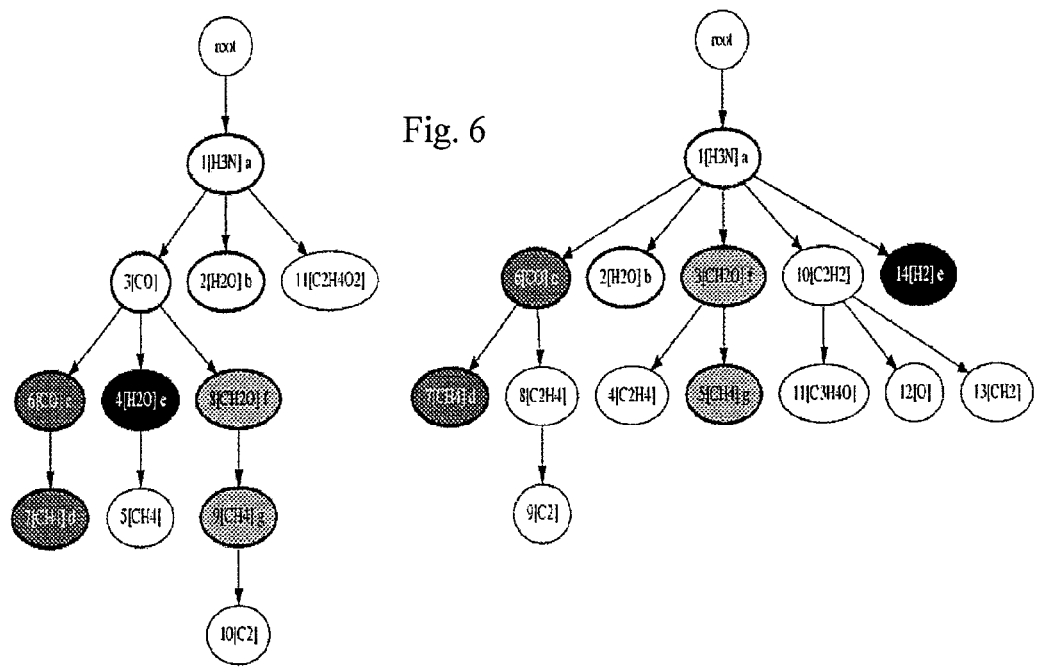
FIG. 6: Optimal local alignment of the fragmentation graphs of dopamine (on the left) and tyramine (on the right)

The result of the local alignment is shown in FIG. 6 (on the left: dopamine and on the right: tyramine). The node designation consists of an index, the total formula, the neutral loss and one letter that indicates the pairwise correspondence in the alignment. The shades of grey visualize this correspondence. Node 3 in the left tree is not colored because it has not an equivalent in the right tree; it has been aligned with a gap. The nodes with a thin frame do not constitute a part of an optimal local alignment.

Figure 7:
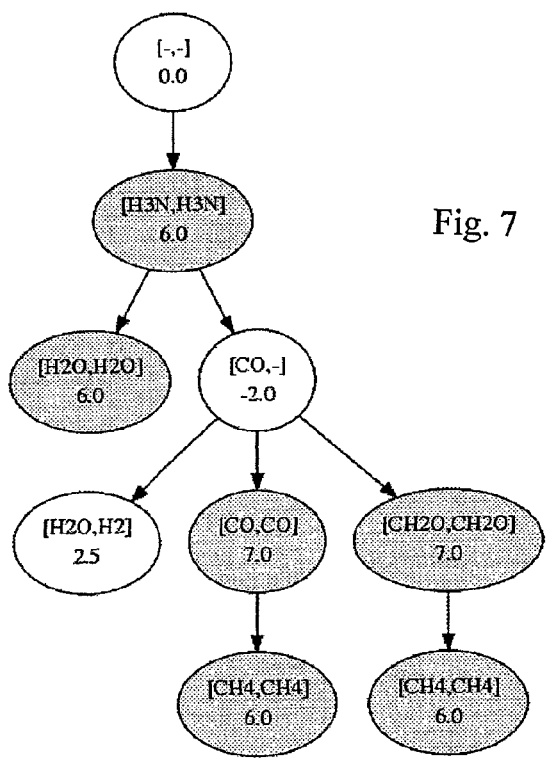
FIG. 7: Overview on the evaluation of the alignment of the fragmentation graphs of dopamine and tyramine

FIG. 7 shows the evaluation of the aligned nodes of the edited fragmentation graphs of dopamine and tyramine. The total formulas of the aligned neutral losses are always given in squared brackets. The evaluation of the corresponding node alignments is indicated below the bracket. Their sum constitutes the total evaluation.

One can see that the structural similarity of the two substances is reflected in the result of the alignment because large areas of the two graphs correlate with each other. Moreover, the additional node "CO" for dopamine that is aligned with a gap makes clear that dopamine possesses an additional hydroxyl group. For this reason, displacements in the separation of correlating carbon atoms are caused which results in the additional loss of CO and not only of an oxygen atom.

Considering the typical application in which one of the two structures is unknown, it could be concluded from the calculated alignment that the structure of the examined substance is very similar to the one of the reference substance and that there is a difference of an oxygen-containing group.

b) Classification of Substances:

In the following, the classification of substances is described by using histidine and 4-hexosyloxybenzoyl choline as an example. Hypothetical fragmentation graphs of 35 further substances have been used for reference purposes.

Like in the first embodiment (determination of structural similarities) fragmentation spectra of the two substances have been measured and hypothetical fragmentation graphs have been calculated and edited. Afterwards, each of the two fragmentation graphs has been locally aligned with all reference graphs and the alignments have been evaluated (the higher the evaluation the higher the degree of the determined similarity). The comparison of two fragmentation graphs followed the procedure that is described in example 1.

The application of the local alignment is only one option. It is also possible to use other methods, either local or global ones, to compare fragmentation graphs.

The results of the comparisons are shown in the tables of FIG. 8 (histidine) and FIG. 9 (4-hexosyloxybenzoyl choline).

It can be seen that the fragmentation graph of 4-hexosyloxybenzoyl choline has a very high degree of local similarity with other cholines (the first 13 hits are choline).

The same applies to histidine, 8 of the best 10 hits are amino acids and the two other ones are amines. This result provides an example of the fact that the introduced approach can be used successfully to classify the two substances examined here into amino acids and cholines.

In addition to this it should be noted that the best hits of this example also have the highest degree of structural similarity with the analyzed substances.

The invention claimed is:

1. Method for identifying chiefly an unknown substance by mass spectrometry comprising the following steps:
   a) recording at least one mass spectrometric fragmentation spectrum (daughter ion spectrum) of the substance to be identified,
   b) determining a fragmentation graph of said substance from the at least one mass spectrometric fragmentation spectrum, wherein in the fragmentation graph fragments of the substance are represented as objects and the fragmentation reactions are represented as links, and
   c) comparing the data of the complete or partial fragmentation graph with reference data for identifying the substance by its structure and/or family and/or its chemical properties.

2. Method according to claim 1, wherein the fragments of the substance are represented as nodes and the fragmentation reactions are represented as edges.

3. Method according to claim 1, wherein the fragmentation graph comprises a mathematical presentation that differs from a typical presentation with nodes and edges.

4. Method according to claim 2, wherein the fragmentation graph is generated automatically.

5. Method according to claim 1, wherein the comparison of the fragmentation graph with the reference data is performed locally and not all objects and links of the fragmentation graph are taken into account for the comparison but only a useful part that has been automatically selected in the comparison procedure.

6. Method according to claims 1, wherein the comparison is realized by pairwise alignments.

7. Method according to claims 1, wherein the comparison is realized by multiple alignments.

8. Method according to claim 1, wherein a computer is used for the comparison.

9. Method according to claim 8, wherein the data of the fragmentation graph are compared with reference data that are stored in an electronic database.

10. Method according to claim 9, wherein the comparison is made by coupling an arrangement for the mass spectrometry, in which the data of the fragmentation graph are generated, with a computer that contains the electronic database.

11. Method according to claim 1, wherein the at least one fragmentation spectrum is generated by a tandem mass spectrometer.

12. Method according to claim 1, wherein the at least one mass-spectrometric fragmentation spectrum is generated by multiple fragmentation ($MS^n$).

13. Method according to claim 1, wherein the fragmentation is performed by collision induced dissociation (CID).

14. Method according to claim 1, further comprising separating components of the substance before the at least one mass spectrometric fragmentation spectrum is recorded.

15. Method according to claim 1, wherein, additionally to the comparison of the data of the fragmentation graphs with reference data, chromatographic retention time and/or electrophoretic thoughput time and/or UV absorption spectra of the substance are used as further comparison criteria for identifying the substance.

16. Method according to claim 1, wherein the mathematical presentation comprises a partial order, a relation or a hierarchy.

17. Method according to claim 14, wherein the separating of components is by liquid chromatography, gas chromatography or capillary electrophoresis.

* * * * *